(12) United States Patent
Schlinker

(10) Patent No.: US 10,221,385 B2
(45) Date of Patent: Mar. 5, 2019

(54) CELL PROCESSING SYSTEM AND METHOD WITH POST-SEPARATION CELL COUNT CONTROL

(71) Applicant: Fenwal, Inc., Lake Zurich, IL (US)

(72) Inventor: Alaina Schlinker, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 38 days.

(21) Appl. No.: 15/589,567

(22) Filed: May 8, 2017

(65) Prior Publication Data

US 2017/0342366 A1   Nov. 30, 2017

Related U.S. Application Data

(60) Provisional application No. 62/342,691, filed on May 27, 2016.

(51) Int. Cl.
| | |
|---|---|
| *C12M 1/36* | (2006.01) |
| *C12M 1/34* | (2006.01) |
| *C12M 1/26* | (2006.01) |
| *C12M 1/00* | (2006.01) |
| *C12N 5/078* | (2010.01) |

(Continued)

(52) U.S. Cl.
CPC .......... *C12M 41/36* (2013.01); *A61M 1/0209* (2013.01); *A61M 1/0281* (2013.01); *A61M 1/265* (2014.02); *C12M 33/14* (2013.01); *C12M 41/44* (2013.01); *C12M 41/48* (2013.01); *C12M 47/04* (2013.01); *C12N 5/0634* (2013.01)

(58) Field of Classification Search
CPC .................................................... C12M 41/48
See application file for complete search history.

(56) References Cited

U.S. PATENT DOCUMENTS

| | | | |
|---|---|---|---|
| 5,053,121 | A | 10/1991 | Schoendorfer et al. |
| 5,194,145 | A | 3/1993 | Schoendorfer |
| 2007/0166291 | A1 | 7/2007 | Benati et al. |

(Continued)

FOREIGN PATENT DOCUMENTS

| | | |
|---|---|---|
| WO | WO 2012/125457 | 9/2012 |
| WO | WO 2012/125470 | 9/2012 |
| WO | WO 2013/043433 | 3/2013 |

OTHER PUBLICATIONS

European Patent Office, Extended European search report, counterpart EP Appl. No. 17170403, dated Oct. 5, 2017.

*Primary Examiner* — Rosanne Kosson
(74) *Attorney, Agent, or Firm* — Cook Alex Ltd.

(57) ABSTRACT

A cell processing system includes a processor connectable to a source container filled with a biological fluid and one or more wash media containers. The processor includes a separator connectable to the source container and a product container, the separator configured to separate the biological fluid from the source container into at least two streams. In addition, a controller is coupled to the processor and configured to: cause the separator to separate the biological fluid into at least two streams, direct one of the at least two streams into the product container, subsequently pause processing of the biological fluid, after pausing, determine a measured cell count in the product container, and add fluid to the product container from the wash media containers as a function of the measured cell count in the product container while the product container is connected to the wash media containers.

20 Claims, 6 Drawing Sheets

(51) Int. Cl.
  *A61M 1/02* (2006.01)
  *A61M 1/26* (2006.01)

(56) References Cited

U.S. PATENT DOCUMENTS

| | | |
|---|---|---|
| 2013/0092630 A1 | 4/2013 | Wegener |
| 2014/0377760 A1* | 12/2014 | Wang ................. G01N 33/5094 435/6.12 |
| 2017/0262601 A1 | 9/2017 | Binninger et al. |
| 2017/0340783 A1 | 11/2017 | Wegener et al. |
| 2018/0015418 A1 | 1/2018 | Binninger et al. |

* cited by examiner

CELL PROCESSING SYSTEM AND METHOD WITH POST-SEPARATION CELL COUNT CONTROL

CROSS-REFERENCE TO RELATED APPLICATIONS

This application claims the benefit of U.S. Provisional Application No. 62/342,691, filed May 27, 2016, which is hereby incorporated herein by reference.

TECHNICAL FIELD

The present disclosure is generally directed to systems and methods for post-separation control based on measured cell count, and to biological fluid processing systems and methods employing such. More particularly, the present disclosure is directed to the controlled processing of biological fluid using a disposable fluid circuit and a reusable processing machine.

BACKGROUND

The processing of biological fluid such as blood or blood components typically involves using a reusable processing machine ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

Conventionally, the biological fluid to be processed is contained in one or more source containers (or bags), which source containers are attached to the disposable fluid circuit and then drawn through the disposable fluid circuit as the biological fluid is processed using the one or more separation devices. Ultimately, cells are collected in another container, referred to as the product container (or bag), which is removed or separated from the disposable fluid circuit when the processing has been completed.

As an initial step in the processing, the operator will sample the biological fluid in the one or more source bags to determine the starting cell concentration of a particular type of cell in the bag. If there is more than one source bag, then the operator will sample each individual bag to determine a starting cell concentration for the cells of interest in that bag. In fact, if there is more than one source bag, the operator will typically calculate a starting number of cells using the starting cell concentrations for each of the source bags.

The starting number of cells of interest is particularly important to the operator as the operator typically will need to input the desired volume in the product bag prior to initiating the processing of the biological fluid, the desired volume selected to achieve a specific concentration of the cells of interest in the product bag. The cell concentration in the product bag is a function of the volume in the product bag and the number of cells present in the product bag. In addition, it will be recognized that the number of cells present in the product bag is a function of the number of cells present in the source bag(s).

To determine the number of cells expected to be present in the product bag, the operator may simply assume full recovery of all of the cells initially present in the product bag. Alternatively, the operator may assume a particular recovery percentage based on historical data. In any event, some assumption is typically made about the effect of processing on the initial number of cells to arrive at the expected number of cells present in the product bag at the end of processing.

Such a method of operation presents several challenges for the operator. For example, the volume within the source bag(s) is often very large, with the consequence that the cell count from the sample taken may not be fully representative of the cell concentration in all regions of the source bag. Further, when there are multiple bags involved, the effects of sampling variations between the bags contribute to further uncertainly in the initial cell count. Even if it were possible to achieve a very representative initial cell count, the assumptions made regarding the effect of the processing on the cell count in the product bag increase the uncertainty of the calculation of the volume required to result in the desired final cell concentration. As such, the final volume selected for the product bag by the operator will likely result in a cell concentration that differs from the desired.

SUMMARY

In one aspect, a cell processing system includes a processor connectable to a source container filled with a biological fluid and one or more wash media containers. The processor includes a separator connectable to the source container and a product container, the separator configured to separate the biological fluid from the source container into at least two streams. In addition, a controller is coupled to the processor and configured to: cause the separator to separate the biological fluid into at least two streams, direct one of the at least two streams into the product container, subsequently pause processing of the biological fluid, after pausing, determine a measured cell count in the product container, and add fluid to the product container from the wash media containers as a function of the measured cell count in the product container while the product container is connected to the wash media containers.

In another aspect, a method for processing a biological fluid includes separating a biological fluid into at least two streams, directing one of the at least two streams into a product container attached to a fluid circuit, and subsequently pausing processing of the biological fluid. The method also includes, after pausing, determining a measured cell count in the product container, and adding fluid to the product container as a function of the measured cell count in the product container while the product container is attached to the fluid circuit.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION

Figure 1:
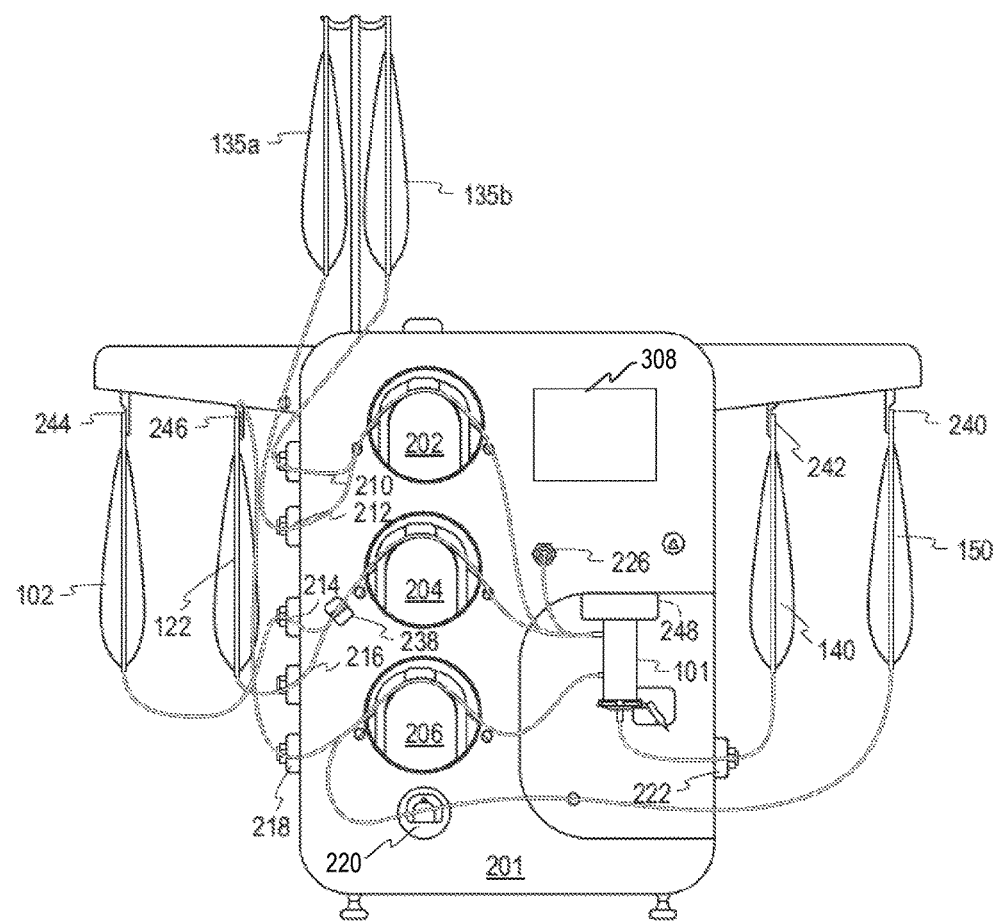
FIG. 1 is a frontal view of a reusable cell processing apparatus with a disposable fluid circuit loaded thereon.
Figure 2:
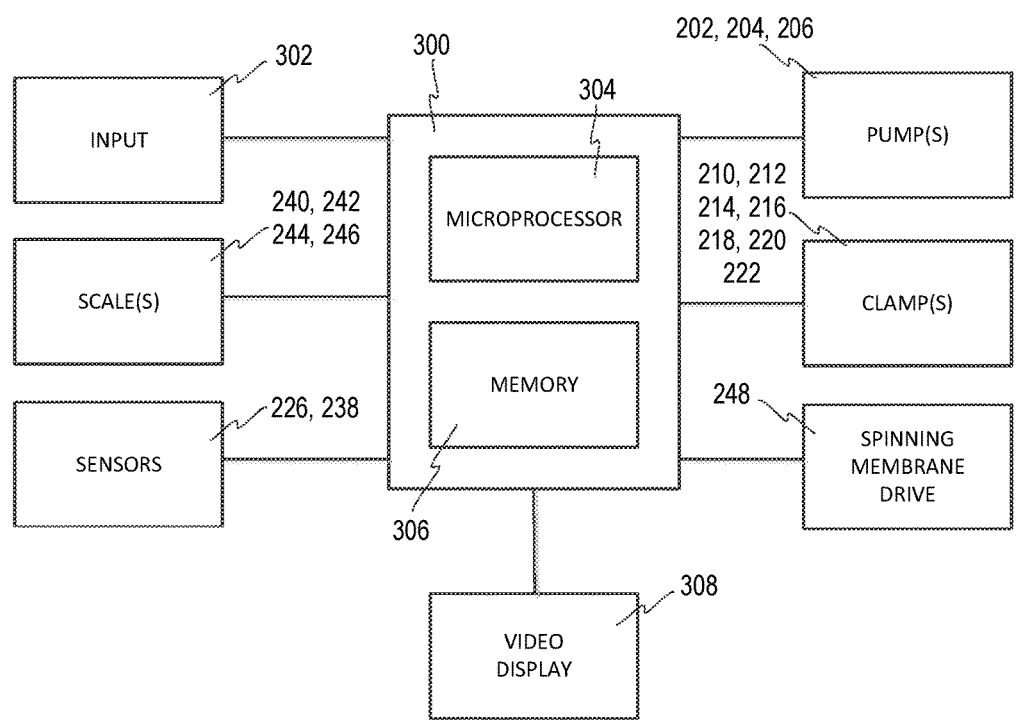
FIG. 2 is a schematic view of the control circuitry of the apparatus of FIG. 1.

As illustrated in FIGS. 1 and 2, a cell processing system includes a processor 100, 200 to receive a biological fluid to be processed, a control unit (or controller) 300 coupled to the processor, the controller 300 configured to operate the processor 100, 200.

As explained in detail below, the processor 100, 200 may include a disposable fluid circuit 100 (see also FIGS. 3 and 5) and reusable hardware 200 (see also FIG. 4). According to the illustrated embodiments, the disposable fluid circuit 100 may include a spinning membrane 101, at least one container 102, 122, 135a, 135b, 140, 150 (of which at least containers 102, 135a, 135b may be initially separate and then connected to the remainder of the circuit 100 at the time of processing), and tubing 106, 120, 128, 132a, 132b, 162, 166, 168 connecting the spinning membrane 101 and the one or more containers 102, 122, 135a, 135b, 140, 150. As is also illustrated, the reusable hardware 200 may include at least one drive 248 to spin the spinning membrane 101, at least one scale 240, 242, 244, 246 to weigh the at least container 102, 122, 140, 150 and contents thereof, and at least one pump 202, 204, 206 to receive the tubing 162, 166, 168 and pump fluid therethrough such as by peristaltic action, although other types of pumps and pumping action may be used.

More particularly and as explained in detail below, the processor is connectable to a source container (e.g., 102 in FIG. 1) filled with a biological fluid and one or more wash media containers (e.g., 135a, 135b in FIG. 1). The processor includes a separator (e.g., 101 in FIG. 1) connectable to the source container and a product container, the separator configured to separate the biological fluid from the source container into at least two streams.

According to embodiments of the system, the controller 300 is configured to cause the separator to separate the biological fluid into at least two streams, direct one of the at least two streams into the product container, subsequently pause processing of the biological fluid, after pausing, determine a measured cell count in the product container, and add fluid to the product container from the wash media containers as a function of the measured cell count in the product container while the product container is connected to the wash media containers. The measured cell count may be determined based on a cell count (e.g., in the form of a cell concentration) received by the controller based on a sample taken from the product container after processing is paused. According to certain embodiments, the controller 300 may include a programmable microprocessor 304, which microprocessor 304 may be programmed to cause the separator to separate the biological fluid into at least two streams, direct one of the at least two streams into the product container, subsequently pause processing of the biological fluid, after pausing, determine a measured cell count in the product container, and add fluid to the product container from the wash media containers as a function of the measured cell count in the product container while the product container is connected to the wash media containers.

In addition, the embodiments herein illustrate a method of processing a biological fluid. The method includes separating a biological fluid into at least two streams, directing one of the at least two streams into a product container attached to a fluid circuit, and subsequently pausing processing of the biological fluid. The method also includes, after pausing, determining a measured cell count in the product container, and adding fluid to the product container as a function of the measured cell count in the product container while the product container is attached to the fluid circuit. Here as well, the measured cell count may be determined based on a cell count (e.g., in the form of a cell concentration) received by the controller based on a sample taken from the product container after processing is paused.

An embodiment of the afore-mentioned system and method may provide one or more of the following advantages. First, the system and method limit the uncertainty as to the cell concentration in the product container by eliminating the need to rely on samples taken from the source container or containers. Specifically, possible uncertainly caused by the large volume of the source container and/or the number of source containers may be eliminated. Further, the system and method limit the uncertainty as to the cell concentration in the product container caused by the assumptions made concerning the processing of the fluid and the possible cell loss occurring during processing. By pausing the system or method and determining a measured cell count in the product container, the calculation of the volume required to produce a specified cell concentration in the product container may be more accurate than when conventional methods are used. Other advantages may also result.

Having thus described the system and method in general terms, the details of the system and method are described in detail.

As mentioned above, the systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

Figure 6:
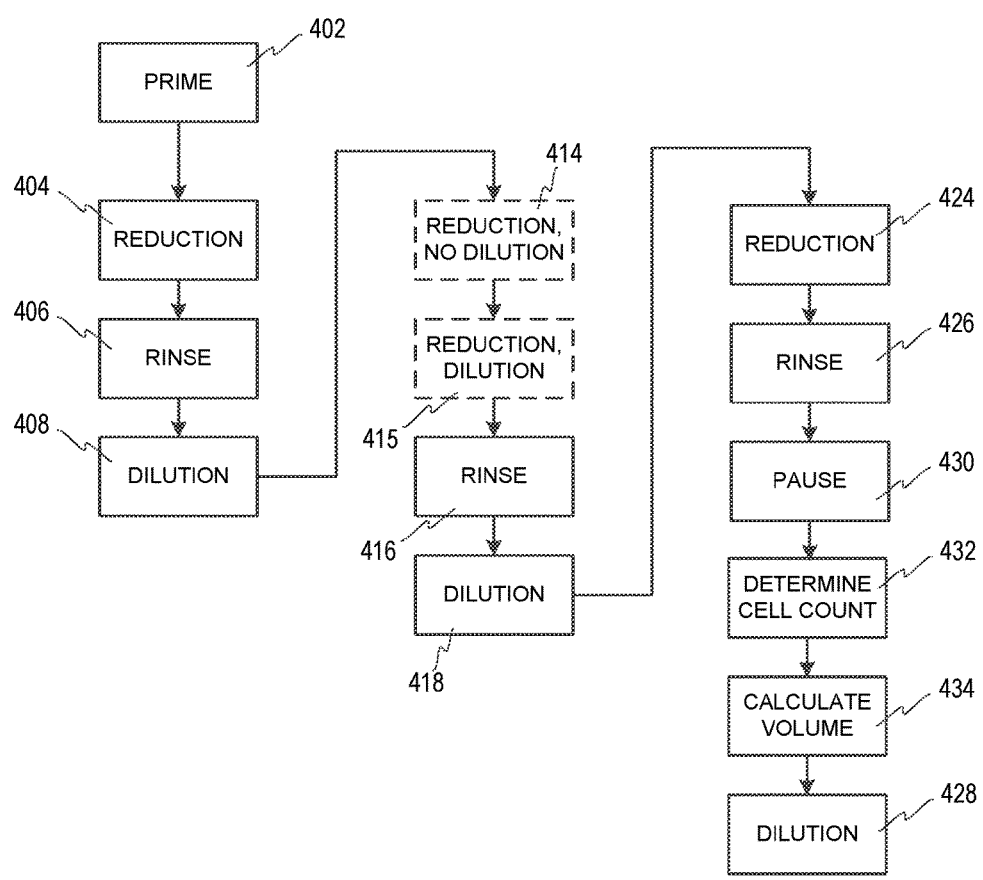
FIG. 6 is a flowchart of one embodiment of a method of operating a reusable cell processing apparatus with a disposable fluid circuit loaded thereon, such as is illustrated in FIG. 1, to process a biological fluid.

The illustrated processing apparatus is typically capable of effecting the separation of a biological fluid that includes biological cells into two or more components or fractions. Thus, the reusable apparatus may generate conditions that allow for the separation of a biological fluid into selected components or fractions. One preferred machine for separating biological fluid into its constituent components or fractions uses a spinning porous membrane. An example of such machine is the Autopheresis C® sold by Fenwal, Inc. of Lake Zurich, Ill., which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which are also incorporated herein in their entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane-covered spinner having an interior collection system disposed within a stationary shell. While a detailed discussion of the separation device is beyond the scope of this application, the spinning membrane separation device is shown in FIGS. 6, 7(a)-7(b) of the reference cited and is discussed below in general terms. In another embodiment, the reusable apparatus may generate a centrifugal field to effect separation.

Figure 3:
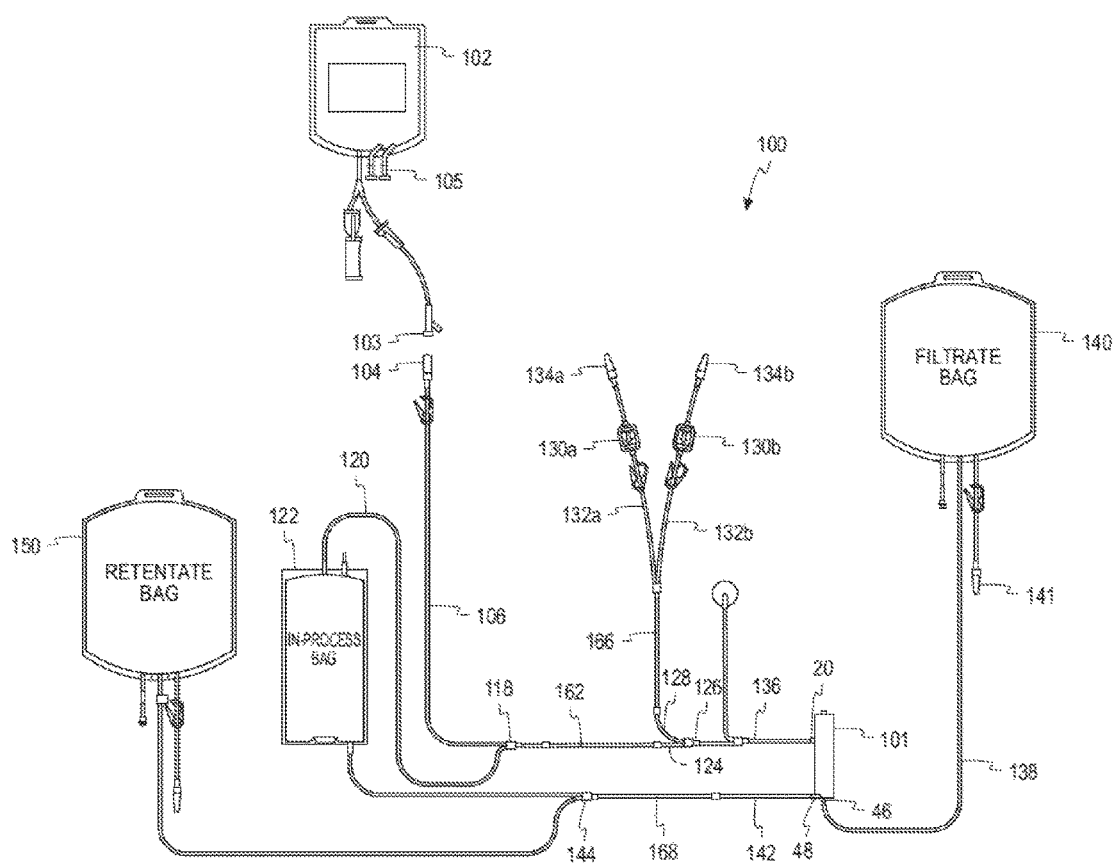
FIG. 3 is a schematic view of one embodiment of a disposable fluid circuit useful in the systems and methods described herein.

Turning now to FIG. 3, the systems described herein include at least one disposable fluid circuit 100 for use in the processing of biological fluid. While the circuits described herein may be used as stand-alone circuits, more preferably, at least two or more disposable fluid circuits are used in combination and in series for the separation, washing, volume reduction and/or other processing of a biological fluid. Circuit 100 may include an integrated separation device, such as, but not limited to, the spinning membrane 101 described above. Circuit 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized poly(vinyl chloride). Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 µm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. No. 5,194,145 and U.S. Pat. No. 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container 140 includes a further connection port 141 for sampling or withdrawing the waste from within the product container.

Separation device 101 preferably includes a second outlet 48 that is connected to tubing segment 142 for directing the desired biological cell/fluid product to the in-process container(s) 122 or the product container 150. To permit this, the other end of tubing segment 142 is connected to branched-connector 144, which branches into and defines a flow path to one or more in-process containers 122 and a flow path to a "final" product container 150. The product container 150 may also include a sampling assembly (not shown).

Figure 4:
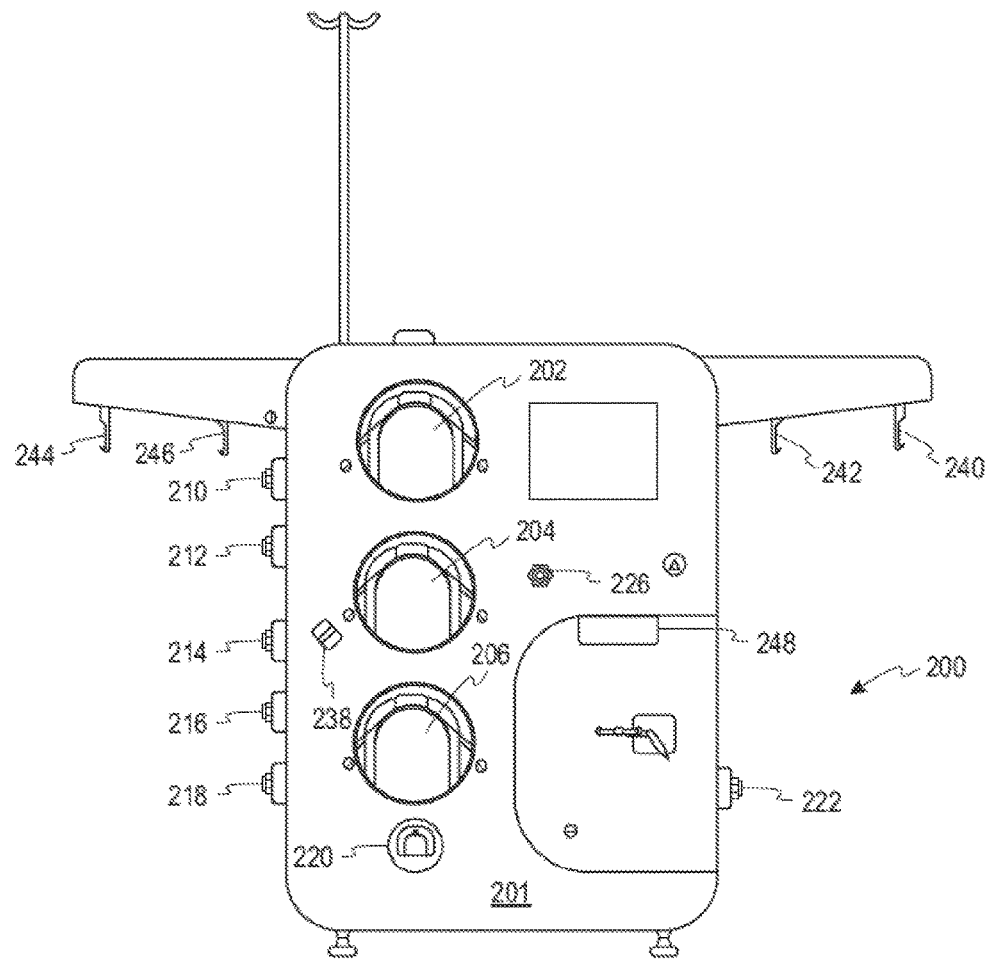
FIG. 4 is a frontal view of the reusable cell processing apparatus.

FIG. 4 shows the front panel 201 of reusable hardware processing apparatus 200, also referred to herein as "hardware". Apparatus 200 may be of compact size suitable for placement on a table top of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container 150, the waste container 140, the source container 102, and the in-process container 122, respectively, may depend and be weighed. The weights of the bags are monitored by weight sensors and recorded during a washing or other procedure. From measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
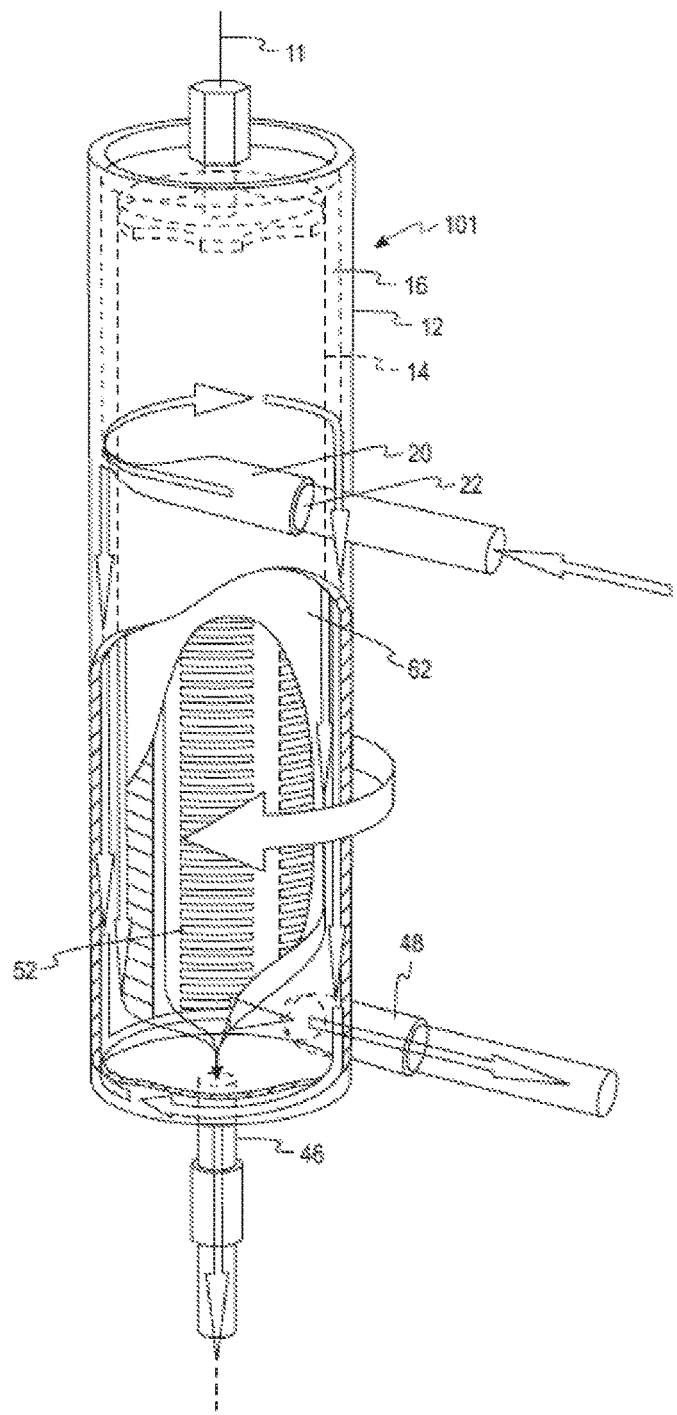
FIG. 5 is a perspective view of a separation/washing device using a spinning membrane.

Turning to FIG. 5, a spinning membrane separation device, generally designated 101, is shown. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 10 microns ($\mu$m), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.8 $\mu$m and a thickness of approximately 150 $\mu$m or greater. Membranes of this type will typically retain all cellular components (e.g., red blood cells, white blood cells) and certain formed blood components, e.g., platelets. In another embodiment, the membrane may be made of a thin (approximately 10 $\mu$m thick) sheet of unsupported polycarbonate, for example, with a pore size of approximately 4.0 $\mu$m. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

Having thus described the processor, including disposable circuit 100 and reusable hardware 200, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor

304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the afore-mentioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing of biological cells, such as mononuclear cells for subsequent therapeutic administration.

In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters using the input 302, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 300 prompts the operator to connect the biological fluid (e.g., 102 of FIG. 3) via a spike connector or sterile connection (e.g., 103, 104 of FIG. 3) and the wash medium (e.g., 135a, 135b of FIG. 3) via a spike connector (e.g., 134a, 134b of FIG. 3). In one embodiment, the biological fluid/cells may be apheresis-collected mononuclear cells, and the wash medium may be a saline solution.

Once the operator confirms that the solutions are connected, the controller 300 primes the disposable set 100. In the embodiment discussed above, the set 100 may be primed with saline, although other bio-compatible aqueous solutions may also be used. The controller 300 then commences processing the biological fluid/cells. The biological fluid/cells is/are transferred from source container (e.g., 102 of FIG. 3) through the set to the spinning membrane separator 101 via the operation of one or more peristaltic pumps 202, 204 and 206. In a similar fashion, the wash medium is delivered from its container (e.g., 135a, 135b of FIG. 3) through the set to the spinning membrane separator 101. The biological cells are collected in either an in-process bag (e.g., 122 of FIG. 3) for additional processing or in a product container (e.g., 150 of FIG. 3), while supernatant is separated and removed to waste container (e.g., 140 of FIG. 3). Once the processing is completed, the controller prompts the operator to sample, seal and remove the product container 150.

A specific embodiment of a method 400 of operating the apparatus 200 is provided in FIG. 6. According to this embodiment, the method 400 of operating the apparatus 200 includes several steps, which steps may be grouped or organized into one or more cycles. For example, reduction, rinse and dilution steps 404, 406, 408 may define a first cycle, reduction, rinse, and dilution steps 414, 415, 416, 418 may define an optional intermediate cycle (which cycle may be omitted, or the steps 414, 415, 416 and/or 418 may be repeated several times to define intermediate cycles—e.g., a 6-cycle procedure may involve the performance of some or all of steps 414-418 a total of 4 times), and reduction, rinse, and dilution steps 424, 426, 428 may define a final cycle. It will be recognized that an apparatus 200 need not perform every step illustrated in FIG. 6, but an apparatus 200 may operate as illustrated in FIG. 6 according to this disclosure.

Preliminary to the first cycle, the controller 300 may cause the apparatus 200 to perform the step of priming the set 100 at block 402. According to this step, wash media from the wash media containers 135a, 135b is transferred to the disposable set 100. Wash media may also be transferred to the source container 102. In fact, a small amount of wash media may be transferred to each of the other containers 102, 122, 140, 150 to ensure that the containers are connected 102, 122, 140, 150. To this end, the controller 300 may cause clamps 214, 216, 218, 220, 222 to open to permit the transfer of fluid to the containers 102, 122, 140, 150.

Once the priming is complete at block 402, the method 400 continues to block 404, where the controller 300 causes the apparatus 200 to perform the first cycle reduction step. According to this step, the controller 300 causes the biological fluid from the source container 102 and wash media from the wash media container(s) 135a, 135b to be transferred to the separator 101. For example, the controller 300 may open clamps 214, 212 (and/or 210) and operate pumps 204, 202 to transfer the fluids from the containers 102, 135a (and/or 135b) to the separator 101. The separator 101 (in conjunction with operation of the drive 248 by controller 300) produces two streams: a first, or retentate, stream that is directed into the in-process container 122, and a second, or filtrate, stream that is directed into the waste container 140. For example, the controller 300 may open clamp 218 and operate pump 206 to cause flow into the in-process container 122 (clamp 220 being closed), and may open clamp 222 to permit flow into the container 140. After the step of block 404 is complete, the controller 300 causes wash media to be passed through the set (i.e., the set is rinsed) and the media is added to the in-process bag 122 at block 406. This may be achieved, for example, by closing clamps 214, 222, while leaving clamps 212 (and/or 210), 218 open and operating pumps 202, 206. After block 406, the method 400 proceeds to block 408, where the controller 300 causes additional wash media to be added to the in-process bag 122. When block 408 is complete, the method 400 passes from the first cycle to the intermediate cycle.

At optional block 414, the controller 300 may cause the apparatus 200 to further reduce the fluid in the in-process bag 122 by transferring the fluid to the separator 101 without additional dilution, and passing the supernatant to the waste container 140 while the cells are returned to the in-process bag 122. For example, the controller 300 opens clamps 216, 218, 222 and operates pumps 204, 206 and drive 248. The controller 300 may continue to cause the apparatus 200 to perform this step until certain user-defined limits have been satisfied. It is also possible that the controller 300 may skip this optional step entirely while operating according to the method 400, and proceed instead to step 415.

At optional block 415, the controller 300 may cause the apparatus 200 to operate such that the feed into the separator 101 is maintained at a constant packed cell volume (PCV). Because cells are being processed from the in-process container 122, concentrated, and then directed back to the in-process container 122, the PCV of the in-process container 122 would continuously increase. To limit or prevent the continuous increase, the controller 300 causes the apparatus 200 is add wash media at increasing rates. As such, the controller may open clamp 212 (and/or 210) and clamps 216, 218, 222 while operating pumps 202, 204, 206 and drive 248, for example.

Once block 415 is complete or bypassed, the controller 300 may cause the apparatus to perform a rinse of the set at block 416 and to add wash media to the in-process bag 122 at block 418. When block 418 is complete, the method 400 passes from the intermediate cycle to the final cycle.

The final cycle begins with block 424, where the controller 300 causes the biological fluid from the in-process container 122 and wash media from the wash media containers 135a, 135b to be transferred to the separator 101. For example, the controller 300 may open clamps 216, 212 (and/or 210) and operate pumps 204, 202 to transfer the fluids from the containers 102, 135a (and/or 135b) to the separator 101. Again, the separator 101 produces two streams: a first, or retentate, stream that is directed into the retentate, or product, container 150 (instead of the in-process container 122), and a second, or filtrate, stream that is directed into the waste container 140. For example, the controller 300 may open clamp 220 and operate pump 206 to cause flow into the product container 150, and may open clamp 222 to permit flow into the container 140. After the step of block 424 is complete, the controller 300 causes wash media to be passed through the set (i.e., the set is rinsed) and the media is added to the product bag 150 at block 426. This may be achieved, for example, by closing clamps 216, 222, while leaving clamps 212 (and/or 210), 220 open and operating pumps 202, 206.

In keeping with the system and method of processing with post-separation cell count control discussed above, the method 400 then proceeds to a block 430, where the controller 300 pauses the processing of the biological fluid. While block 430 is illustrated as subsequent to the rinse performed at block 426, it may be possible that the pause occurs prior to the rinse at block 426. Preferably, the pause at block 430 occurs after the rinse to maximize the number of cells of interest that will be present in the product container 150. It will be recognized that, because of the configuration of the circuit 100 illustrated, the subsequent action at block 428 may cause cells to be transferred to the product container 150 from the circuit 100. As such, it is preferred to pause the processing at block 430 after the rinse at block 426, but it is not essential that this is performed, as the benefits of the system and method over conventional systems and methods still may be obtained even if the pause occurred prior to the rinse at block 426.

As to how the controller 300 determines when to pause the processing of the biological fluid, according to one embodiment, the controller 300 may be configured to set a volume threshold for the product container 150, measure a volume in the product container 150, and pause processing of the biological fluid when the volume in the product container 150 exceeds the volume threshold. The controller 300 may receive the volume threshold for the product container 150 from the operator via the input 302; alternatively, the volume threshold may be set by an administrator (i.e., a user that has a special status relative to inputs received by the controller 300) and may be not modifiable by the operator. According to certain embodiments, the volume threshold may be received prior to separation of the biological fluid into two streams in the separator 101, and more particularly even before the set 100 is primed in block 402. The controller 300 may determine the volume in the product container 150, for example, by weighing the product container 150 using the scale 240.

The controller 300 may maintain the processor 100, 200 in the paused state for a predetermined period. Alternatively, the controller 300 may maintain the processor 100, 200 in the paused state until the controller 300 receives an indication via the input 302, for example, that the operator is ready to continue processing. The indication may be in the form of an instruction (e.g., the depression of a specific key on a key pad or keyboard, for example), or the indication may be in the form of data required to perform the subsequent actions of the method 400. In particular, the data may relate to the measured cell count in the product container 150.

According to some embodiments, the controller 300 pauses the processing to permit the operator to take or remove a sample of the material in the product container 150. Based on this sample the operator may determine a cell count, which may be in the form of a cell concentration, for the material in the product container 150. The operator may then enter this data using the input 302, the controller 300 may receive the data via the input 302, and the controller may use the data to determine the measured cell count at block 432. The controller 300 may use the measured cell count in performing the further actions of the method 400. As an alternative to receiving the cell count from the operator via the input 302, the processor 100, 200 may include a sensor that is associated with the product container 150, which sensor may be used to make a determination of the cell count within the product container 150. According to such an alternative, the controller 300 may determine the measured cell count automatically via the sensor, without need for operator intervention. The controller 300 may still pause the processing to limit the uncertainty that the measured cell count obtained using the sensor would not be representative of the material in the product container 150.

The method 400 continues to block 434, where the controller calculates a volume of fluid to add to the product container 150 so that the cells of interest in the product container 150 are at a desired cell concentration. The controller 300 may receive the desired cell concentration from the operator via the input 302, or the desired cell concentration may be set by an administrator such that it is not modifiable by the operator. In particular, the calculation of the fluid volume may be a function of the measured cell count in the product container 150 determined at block 432 and the desired final cell concentration in the product container 150. For example, the fluid volume may be calculated by dividing the measured cell count by the desired final cell concentration. By performing the calculation using the cell count determined at block 432 after the processing 430 is paused post-separation (at block 424), much of the uncertainty caused when the conventional methods outlined above are used may be limited or eliminated.

The method 400 next proceeds to block 428, where the calculated fluid volume is added to the product container 150, for example from the one or more wash media containers 135a, 135b. When block 428 is complete, the method 400 may continue with other steps, such as incubation, as may be desired before the product bag 150 is sampled, separated from the fluid circuit 100, and sealed.

While the method 400 includes three cycles, with the actions of blocks 430, 432, 434, 428 being carried out during the final cycle, it will be recognized that the actions of blocks 430, 432, 434, 428 could be carried out instead during a single cycle performed on a processor 100, 200. In addition, the method 400 may be carried out on an apparatus that performs separation using a separator other than the spinning membrane separator 101 illustrated herein. Further, the pause 430 may even occur before a rinse step (426) is conducted, or for that matter, before the separation step 424 is carried out on all of the material contained in the source container 102. That is, the threshold condition for pausing processing may be set such that only part of the separation has been conducted. Even in such a circumstance, the system and method may be described as conducting a post-separation cell count control on the cells of interest in the product container 150. Moreover, while the above system and method eliminate the need to take and analyze a sample of the fluid in the source container, the system and method are not inconsistent with taking and analyzing a sample of fluid in the source container, rather being inconsistent with using that sample to determine the fluid volume added to the product container to achieve a desired final cell concentration.

The systems and methods described herein may be effective, for example, in the washing of cells such as red blood cells and/or white blood cells. In one example of red cell washing, stored red blood cells may be washed to remove accumulated free hemoglobin, spent storage solution, or extracellular components. The washing solution may be sterile docked or otherwise included in the closed system of the disposable processing set of the type described above. The treated cells may then be washed with the washing solution such as saline, Adsol or E-Sol (the latter of which are red blood cell storage solutions and generally comprise dextrose, mannitol and a buffer) to reconstitute the red blood cells for subsequent storage and transfusion.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

Thus, an improved method and system have been disclosed for the processing of biological cells. The description provided above is intended for illustrative purposes only and is not intended to limit the scope of the invention to any specific method, system, or apparatus, or device described herein except as may be explicitly delineated above.

In conclusion, according to one aspect, a cell processing system includes a processor connectable to a source container filled with a biological fluid and one or more wash media containers. The processor includes a separator connectable to the source container and a product container, the separator configured to separate the biological fluid from the source container into at least two streams. In addition, a controller is coupled to the processor and configured to: cause the separator to separate the biological fluid into at least two streams, direct one of the at least two streams into the product container, subsequently pause processing of the biological fluid, after pausing, determine a measured cell count in the product container, and add fluid to the product container from the wash media containers as a function of the measured cell count in the product container while the product container is connected to the wash media containers.

According to certain aspects of the system, the controller is additionally configured to calculate a fluid volume to add to the product container as a function of the measured cell count in the product container and a desired final cell concentration in the product container prior to adding fluid. The controller may be configured to add the fluid volume to the product container from the one or more wash media containers.

The system may include an input, and the controller may be configured to receive the measured cell count via the input. The measured cell count may be in the form of a measured cell concentration in the product container.

According to further aspects of the system, the controller may be configured to set a volume threshold for the product container, measure a volume in the product container, and pause processing of the biological fluid when the volume in the product container exceeds the volume threshold.

The controller may include a microprocessor, and the microprocessor may be programmed to cause the separator to separate the biological fluid into at least two streams, direct one of the at least two streams into the product container, subsequently pause processing of the biological fluid, after pausing, determine a measured cell count in the product container, and add fluid to the product container from the one or more wash media containers as a function of the measured cell count in the product container while the product container is connected to the wash media containers.

According to other aspects of the system, the processor may include a disposable fluid circuit and reusable hardware. The disposable fluid circuit may include a spinning membrane separation device that defines the separator.

According to another aspect, a method for processing a biological fluid includes separating a biological fluid into at least two streams, directing one of the at least two streams into a product container attached to a fluid circuit, and subsequently pausing processing of the biological fluid. The method also includes, after pausing, determining a measured cell count in the product container, and adding fluid to the product container as a function of the measured cell count in the product container while the product container is attached to the fluid circuit According to certain aspects of the method, the method may include, prior to adding fluid, calculating a fluid volume to add to the product container as a function of the measured cell count in the product container and a desired final cell concentration in the product container. The step of adding fluid to the product container may include adding the fluid volume calculated as a function of the measured cell count in the product container and the desired final cell concentration in the product container.

According to additional aspects, determining the measured cell count may include receiving the measured cell count based on a sample taken from the product container. Further, the measured cell count in the product container may be in the form of a measured cell concentration in the product container.

According to further aspects of the method, the method may include setting a volume threshold for the product container, measuring a volume in the product container, and pausing processing of the biological fluid when the volume in the product container exceeds the volume threshold. The method may also include receiving the volume threshold for the product container prior to setting the volume threshold and prior to separating the biological fluid into two streams. Moreover, measuring a volume in the product container may include weighing the product container.

According to aspects of the method, separating a biological fluid into two streams may include introducing the biological fluid into a separator including a cylindrical housing and an internal member, the cylindrical housing having an interior surface and the internal member having an exterior surface, the surfaces defining a gap therebetween and at least one of the surfaces including a porous membrane, and rotating at least one or both of the cylindrical housing and the internal member.

According to still further aspects of the method, the method may include separating the product container from the fluid circuit after adding fluid to the product container as a function of a measured cell count in the product container, and sealing the product container after separating the product container from the fluid circuit.

The invention claimed is:

1. A system for processing biological cells, the system comprising:
   (a) a processor connectable to
   (b) a source container filled with
   (c) a biological fluid and
   (d) one or more wash medium containers, the processor including
   (e) a separator connectable to the source container and
   (f) a product container, the separator configured to separate the biological fluid from the source container into at least two streams; and
   (g) a controller coupled to the processor, the controller configured to:
     (i) cause the separator to separate the biological fluid into at least two streams;
     (ii) direct one of the at least two streams into the product container;
     (iii) subsequently pause processing of the biological fluid;
     (iv) after pausing, determine a measured cell count in the product container; and
     (v) add fluid to the product container from the one or more wash medium containers as a function of the measured cell count in the product container while the product container is connected to the wash medium containers.

2. The system according to claim 1, wherein the controller is additionally configured to calculate a fluid volume to add to the product container as a function of the measured cell count in the product container and a desired final cell concentration in the product container prior to adding fluid.

3. The system according to claim 2, wherein the controller is configured to add the fluid volume to the product container from the one or more wash media containers.

4. The system according to claim 1, further comprising an input, the controller being configured to receive the measured cell count via the input.

5. The system according to claim 1, wherein the measured cell count is in the form of a measured cell concentration in the product container.

6. The system according to claim 1, wherein the controller is further configured to:
   (i) set a volume threshold for the product container;
   (ii) measure a volume in the product container; and
   (iii) pause processing of the biological fluid when the volume in the product container exceeds the volume threshold.

7. The system according to claim 1, wherein the controller comprises a microprocessor, the microprocessor programmed to:
   (i) cause the separator to separate the biological fluid into at least two streams;
   (ii) direct one of the at least two streams into the product container;
   (iii) subsequently pause processing of the biological fluid;
   (iv) after pausing, determine a measured cell count in the product container; and
   (v) add fluid to the product container from the one or more wash media containers as a function of the measured cell count in the product container while the product container is connected to the wash media containers.

8. The system according to claim 1, wherein the processor comprises a disposable fluid circuit and reusable hardware.

9. The system according to claim 8, wherein the disposable fluid circuit comprises a spinning membrane separation device that defines the separator.

10. A method for processing a biological fluid with the system of claim 1, the method comprising:
    a), separating a biological fluid info at least two streams;
    b) directing one of the at least two streams into a product container attached to a fluid circuit;
    c) subsequently pausing processing of the biological fluid;
    d) after pausing, determining a measured cell count in the product container; and
    e) adding fluid to the product container as a function of the measured cell count in the product container while the product container is attached to the fluid circuit.

11. The method according to claim 10, further comprising, prior to adding fluid, calculating a fluid volume to add to the product container as a function of the measured cell count in the product container and a desired final cell concentration in the product container.

12. The method according to claim 11, wherein the step of adding fluid to the product container comprises adding the fluid volume calculated as a function of the measured cell count in the product container and the desired final cell concentration in the product container.

13. The method according to claim 10, wherein determining the measured cell count comprises receiving the measured cell count based on a sample taken from the product container.

14. The method according to claim 10, wherein the measured cell count in the product container is in the form of a measured cell concentration in the product container.

15. The method according to claim 10, further comprising:
    a) setting a volume threshold for the product container;
    b) measuring a volume in the product container; and
    c) pausing processing of the biological fluid when the volume in the product container exceeds the volume threshold.

16. The method according to claim 15, further comprising receiving the volume threshold for the product container prior to setting the volume threshold and prior to separating the biological fluid into two streams.

17. The method according to claim 15, wherein measuring a volume in the product container comprises weighing the product container.

18. The method according to claim 10, wherein separating a biological fluid into two streams comprises:
    a) introducing the biological fluid into a separator comprising a cylindrical housing and an internal member, the cylindrical housing having an interior surface and the internal member having an exterior surface, the surfaces defining a gap therebetween and at least one of the surfaces including a porous membrane; and
    b) rotating at least one or both of the cylindrical housing and the internal member.

19. The method according to claim 10, further comprising separating the product container from the fluid circuit after adding fluid to the product container as a function of a measured cell count in the product container.

20. The method according to claim 19, further comprising sealing the product container after separating the product container from the fluid circuit.

* * * * *

UNITED STATES PATENT AND TRADEMARK OFFICE
CERTIFICATE OF CORRECTION

PATENT NO. : 10,221,385 B2
APPLICATION NO. : 15/589567
DATED : March 5, 2019
INVENTOR(S) : Alaina Schlinker It is certified that error appears in the above-identified patent and that said Letters Patent is hereby corrected as shown below:

In the Claims

In Column 16, Line 45, in Claim 10, delete "info" and insert --into--

Signed and Sealed this
Sixteenth Day of July, 2019

Andrei Iancu
*Director of the United States Patent and Trademark Office*